United States Patent
Kwon et al.

(10) Patent No.: US 9,255,959 B2
(45) Date of Patent: Feb. 9, 2016

(54) TEST APPARATUS FOR SEMICONDUCTOR PACKAGE

(71) Applicant: Samsung Electronics Co., Ltd., Suwon-Si, Gyeonggi-Do (KR)

(72) Inventors: Chan-Sik Kwon, Asan-si (KR); Seok-Won Jeong, Daejeon (KR); Jae-Ho Choi, Cheonan-si (KR); Jun-Young Ko, Cheonan-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 325 days.

(21) Appl. No.: 13/961,201

(22) Filed: Aug. 7, 2013

(65) Prior Publication Data

US 2014/0062496 A1 Mar. 6, 2014

(30) Foreign Application Priority Data

Sep. 6, 2012 (KR) .................. 10-2012-0098819

(51) Int. Cl.
*G01N 23/04* (2006.01)
*G01R 31/26* (2014.01)
*G01R 31/28* (2006.01)
*G01R 31/308* (2006.01)

(52) U.S. Cl.
CPC ............ *G01R 31/2607* (2013.01); *G01N 23/04* (2013.01); *G01R 31/2896* (2013.01); *G01R 31/308* (2013.01)

(58) Field of Classification Search
CPC ... G01N 23/04; G01N 23/18; G01R 31/2607; G01R 31/2812; G01R 31/2896; G01R 31/302
See application file for complete search history.

(56) References Cited

U.S. PATENT DOCUMENTS

| 5,750,997 A * | 5/1998 | Matsuda .............. G01R 31/308 250/341.1 |
| 5,848,122 A * | 12/1998 | Kurtz .................... G01R 31/265 378/79 |
| 6,553,546 B1 * | 4/2003 | Murakami ........... G01R 31/311 324/501 |
| 6,855,930 B2 * | 2/2005 | Okuda ................. G01N 23/225 250/310 |
| 7,666,690 B2 | 2/2010 | Lee et al. |
| 2008/0037859 A1 | 2/2008 | Ohkura et al. |
| 2008/0164413 A1 | 7/2008 | Shibayama |
| 2011/0297829 A1 * | 12/2011 | Altmann .................. G01N 1/00 250/332 |
| 2014/0062521 A1 * | 3/2014 | Yamada ............... G01R 31/046 324/762.01 |

FOREIGN PATENT DOCUMENTS

| JP | 2008145245 A | 6/2008 |
| KR | 100480490 B1 | 4/2005 |
| KR | 20100055974 A | 5/2010 |
| KR | 20100067326 A | 6/2010 |
| KR | 100992702 B1 | 11/2010 |
| KR | 101003693 B1 | 12/2010 |
| KR | 101092206 | 6/2011 |
| KR | 101066858 B1 | 9/2011 |
| KR | 101133503 B1 | 4/2012 |

* cited by examiner

*Primary Examiner* — Glen Kao
(74) *Attorney, Agent, or Firm* — Harness, Dickey & Pierce, P.L.C.

(57) ABSTRACT

A test apparatus for a semiconductor package comprising an X-ray analyzer acquiring an X-ray image of the semiconductor package and detecting a thickness of the semiconductor package from the X-ray image, and a thermal reaction analyzer applying a voltage to the semiconductor package and detecting a failure position of the semiconductor package using a surface temperature of the semiconductor package and the thickness of the semiconductor package may be provided.

20 Claims, 8 Drawing Sheets

TEST APPARATUS FOR SEMICONDUCTOR PACKAGE

CROSS-REFERENCE TO RELATED APPLICATIONS

This application is based on and claims priority under 35 U.S.C. §119 to Korean Patent Application No. 10-2012-0098819, filed on Sep. 6, 2012 in the Korean Intellectual Property Office, the disclosure of which is hereby incorporated by reference in its entirety.

BACKGROUND

1. Field

Example embodiments relate to test apparatuses for a semiconductor package.

2. Description of the Related Art

A semiconductor package is provided by mounting a semiconductor chip on a package substrate, performing electrical connection using wires, and sealing the package with a sealing resin such as EMC or the like. A test apparatus for a semiconductor package detects failure that occurs due to open or short of signal lines of the package substrate or the semiconductor chip of the semiconductor package.

SUMMARY

The present inventive concepts provide test apparatuses for a semiconductor package that can accurately detect a failure position.

The present inventive concepts provide test apparatuses for a semiconductor package that can reduce a detection time of a failure position.

According to an example embodiment, a test apparatus for a semiconductor package includes an X-ray analyzer configured to acquire an X-ray image of the semiconductor package and detect a thickness of the semiconductor package from the X-ray image, and a thermal reaction analyzer configured to apply voltages to the semiconductor package and detect a failure position of the semiconductor package using a surface temperature of the semiconductor package and the detected thickness of the semiconductor package.

The X-ray analyzer may include an image processor configured to detect the thickness of the semiconductor package using a density of an area of the semiconductor package in the X-ray image.

The semiconductor package may include at least one layer, and the image processor may be configured to detect a thickness of the at least one layer using density information of the at least one layer in the X-ray image.

The thermal reaction analyzer may include a failure detector configured to detect vertical coordinates of the failure position using a phase difference between the voltages applied to the semiconductor package and the surface temperature of the semiconductor package.

The thermal reaction analyzer may include an infrared scope configured to acquire a thermographic image on a surface of the semiconductor package, and the failure detector configured to detect the surface temperature of the semiconductor package from the thermographic image.

The failure detector may be configured to detect the vertical coordinates of the failure position using a thermal diffusion coefficient of the semiconductor package.

The thermal reaction analyzer may include an infrared scope configured to acquire a thermographic image on the surface of the semiconductor package, and a failure detector configured to detect horizontal coordinates of the failure position from the thermographic image.

The failure detector may be configured to detect coordinates of a pixel having a maximum pixel value in the thermographic image as the horizontal coordinates of the failure position.

The X-ray image may be a three-dimensional X-ray image of the semiconductor package.

According to an example embodiment, a test apparatus for a semiconductor package includes an X-ray analyzer configured to detect a thickness of the semiconductor package, and a thermal reaction analyzer configured to detect a failure position of the semiconductor package, wherein the X-ray analyzer includes an X-ray scope configured to acquire an X-ray image of the semiconductor package, an image processor configured to detect a thickness of the semiconductor package from the X-ray image, and a display unit configured to display the X-ray image on which the failure position is shown, and wherein the thermal reaction analyzer includes a voltage supply device configured to apply voltages to the semiconductor package, an infrared scope configured to acquire a thermographic image on a surface of the semiconductor package, and a failure detector configured to detecting vertical coordinates of the failure position using the detected thickness of the semiconductor package and a phase difference between the voltages applied to the semiconductor package and a surface temperature of the semiconductor package and detect horizontal coordinates of the failure position from the thermographic image.

The semiconductor package may include at least one layer, and the image processor may be configured to detect a thickness of the at least one layer using density information of the at least one layer in the X-ray image.

The failure detector may be configured to detect the surface temperature of the semiconductor package from the thermographic image.

The failure detector may be configured to detect the vertical coordinates of the failure position using a thermal diffusion coefficient of the semiconductor package.

The failure detector may be configured to detect coordinates of a pixel having a maximum pixel value in the thermographic image as the horizontal coordinates of the failure position.

The X-ray image may be a three-dimensional X-ray image of the semiconductor package.

According to an example embodiment, a test apparatus for a semiconductor package includes an X-ray analyzer configured to detect at least one of a thickness of the semiconductor package and thicknesses of layers of the semiconductor package using a X-ray image of the semiconductor package and density information of the layers, and a thermal reaction analyzer configured to apply voltages to the semiconductor package and detect a failure position of the semiconductor package using a surface temperature of the semiconductor package and the detected thickness transmitted from the X-ray analyzer.

The thermal reaction analyzer may include an infrared scope configured to acquire a thermographic image of a surface of the semiconductor package, and a failure detector configured to detect a horizontal coordinate and a vertical coordinate of the failure position of the semiconductor package.

The failure detector may be configured to detect the horizontal coordinate of the failure position from the thermographic image of the surface of the semiconductor package, and the failure detector may be configured to detect a vertical coordinate of the failure position using a phase difference between the voltages applied to the semiconductor package and the surface temperature of the semiconductor device.

The failure detector may be configured to detect a vertical coordinate of the failure position using thermal diffusion coefficient information of layers forming the semiconductor package and a phase difference between the voltages applied to the semiconductor package and the surface temperature of the semiconductor device.

The X-ray analyzer may include an X-ray scope configured to acquire at least one of a two-dimentional and a three-dimensional X-ray image, and an image processor configured to detect the at least one of a thickness of the semiconductor package and thicknesses of layers of the semiconductor package using the density information of the layers. Additional advantages, subjects, and features of the inventive concepts will be set forth in part in the description which follows and in part will become apparent to those having ordinary skill in the art upon examination of the following or may be learned from practice of the inventive concepts.

BRIEF DESCRIPTION OF THE DRAWINGS

The above and other subjects, features and advantages of the present inventive concepts will be more apparent from the following detailed description taken in conjunction with the accompanying drawings, in which.

DETAILED DESCRIPTION

Figure 1:
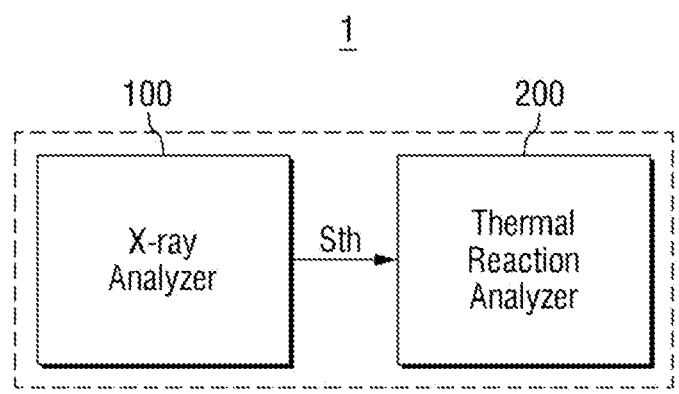
FIG. 1 is a schematic block diagram illustrating the configuration of a test apparatus for a semiconductor package according to an example embodiment.

The present inventive concepts will now be described more fully hereinafter with reference to the accompanying drawings, in which example embodiments are shown. The inventive concepts may, however, be embodied in different forms and should not be construed as limited to the example embodiments set forth herein. Rather, these example embodiments are provided so that this disclosure will be thorough and complete, and will fully convey the scope of the inventive concepts to those skilled in the art. The same reference numbers indicate the same components throughout the specification. In the attached figures, the thicknesses of layers and regions are exaggerated for clarity.

It will also be understood that when a layer is referred to as being "on" another layer or substrate, it can be directly on the other layer or substrate, or intervening layers may also be present. In contrast, when an element is referred to as being "directly on" another element, there are no intervening elements present.

Spatially relative teams, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

The use of the terms "a" and "an" and "the" and similar referents in the context of describing the inventive concepts (especially in the context of the following claims) are to be construed to cover both singular and plural, unless otherwise indicated herein or clearly contradicted by context. The terms "comprising," "having," "including," and "containing" are to be construed as open-ended terms (i.e., meaning "including, but not limited to"), unless otherwise noted.

Unless defined otherwise, all technical and scientific terms used herein have the same meaning as commonly understood by one of ordinary skill in the art to which these inventive concepts belong. It is noted that the use of any and all examples, or example terms provided herein is intended merely to better illuminate the inventive concepts and is not a limitation on the scope of the inventive concepts unless otherwise specified. Further, unless defined otherwise, all terms defined in generally used dictionaries may not be overly interpreted.

The present inventive concepts will be described with reference to perspective views, cross-sectional views, and/or plan views, in which example embodiments of the inventive concepts are shown. Thus, the profile of an example view may be modified according to manufacturing techniques and/or allowances. That is, the example embodiments are not intended to limit the scope of the present inventive concepts, but cover all changes and modifications that can be caused due to a change in manufacturing process. Thus, regions shown in the drawings are illustrated in schematic form and the shapes of the regions are presented simply by way of illustration and not as a limitation.

Hereinafter, with reference to the accompanying drawings, embodiments of the present inventive concepts will be described in detail. Hereinafter, a multi-chip package, in which two semiconductor chips are laminated on a package substrate, is exemplified. However, the present inventive concepts is not limited thereto, and it is apparent to those of ordinary skill in the technical field to which the present inventive concepts pertain that the present inventive concepts can be applied to a single chip package and various kinds of semiconductor packages.

FIG. 1 is a schematic block diagram illustrating the configuration of a test apparatus for a semiconductor package according to an example embodiment.

Referring to FIG. 1, a test apparatus 1 for a semiconductor package includes an X-ray analyzer 100 and a thermal reaction analyzer 200.

The X-ray analyzer 100 may acquire an X-ray image of a semiconductor package, and may detect the thickness of the semiconductor package from the X-ray image of the semiconductor package. The X-ray analyzer 100 may transmit the detected thickness information Sth of the semiconductor package to the thermal reaction analyzer 200. The detailed configuration of the X-ray analyzer 100 will be described with reference to FIG. 2.

The thermal reaction analyzer 200 may receive the thickness information Sth of the semiconductor package from the X-ray analyzer 100. The thermal reaction analyzer 200 may apply a voltage to the semiconductor package, and may detect a failure position F of the semiconductor package using a surface temperature of the semiconductor package and the thickness information of the semiconductor package (e.g., thicknesses of at least one layer constituting the semiconductor package). The detailed configuration of the thermal reaction analyzer 200 will be described with reference to FIG. 3 later.

Figure 2:
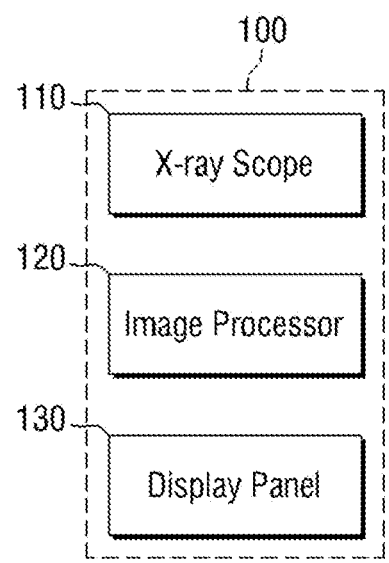
FIG. 2 is a schematic block diagram illustrating the configuration of an X-ray analyzer of FIG. 1.

Hereinafter, referring to FIG. 2, the configuration of the X-ray analyzer of FIG. 1 will be described in more detail. FIG. 2 is a schematic block diagram illustrating the configuration of the X-ray analyzer of FIG. 1.

Referring to FIG. 2, the X-ray analyzer 100 includes an X-ray scope 110, an image processor 120, and a display panel 130.

The X-ray scope 110 may acquire an X-ray image of a semiconductor package. The X-ray image of the semiconductor package may be a two-dimensional (2D) or three-dimensional (3D) image of the semiconductor package.

The X-ray image of the semiconductor package may include, for example, a CT (Computer Tomography) image of the semiconductor package. If the semiconductor package is a multi-chip package in which multiple semiconductor chips are laminated, the CT image of the semiconductor package may include single-layer images for respective layers. The single-layer images for the respective layers may be reconfigured as a 3D X-ray image of the semiconductor package.

The image processor 120 may detect the thickness of the semiconductor package from the X-ray image of the semiconductor package. The image processor 120 may detect the thickness of an area of the X-ray image of the semiconductor package using the density information of the semiconductor package. The X-ray image may be captured on the basis of the penetration degree of X-rays that penetrate an object to be photographed, and the penetration degree of the X-rays may be determined by the density of the object to be photographed. Hereinafter, in the case where the X-ray image of the semiconductor package is digitalized, the density value may correspond to a pixel value of the digitalized X-ray image. A method of detecting the thickness of the semiconductor package will be described in more detail with reference to FIG. 4.

The display panel 130 may display the X-ray image of the semiconductor package.

Figure 3:
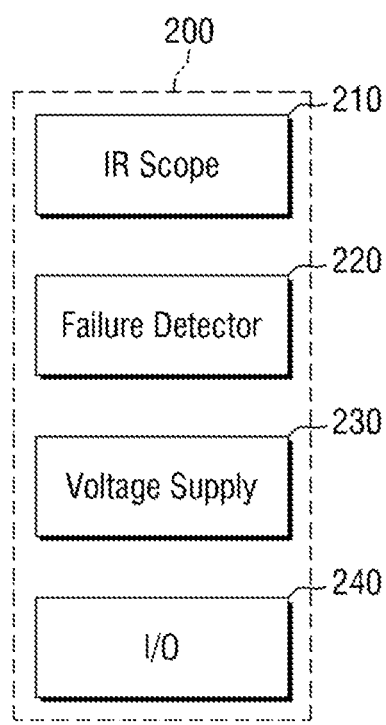
FIG. 3 is a schematic block diagram illustrating the configuration of a thermal reaction analyzer of FIG. 1.

Hereinafter, referring to FIG. 3, the configuration of the thermal reaction analyzer of FIG. 1 will be described in more detail. FIG. 3 is a schematic block diagram illustrating the configuration of a thermal reaction analyzer of FIG. 1.

Referring to FIG. 3, the thermal reaction analyzer 200 includes an infrared (IR) scope 210, a failure detector 220, a voltage supply device 230, and an input/output (I/O) device 240.

The infrared scope 210 may acquire a thermographic image of the semiconductor package. The infrared scope 210 may measure infrared energy that is emitted from an object to be photographed, and may acquire a thermographic image that shows temperature distribution of the object to be photographed. The infrared scope 210 may acquire the thermographic image that shows the temperature distribution of the surface of the semiconductor package. Here, the surface of the semiconductor package may include an upper surface and respective side surfaces of the semiconductor package.

The thermographic image of the surface of the semiconductor package may be displayed with colors that are discriminated in multiple steps depending on the temperature distribution of the semiconductor package. For example, an area having the highest temperature on the thermographic image of the surface of the semiconductor package may be displayed with red color, and an area having the lowest temperature may be displayed with blue color. Accordingly, a pixel displayed with red color may have RGB values of (255, 0, 0), and a pixel displayed with blue color may have RGB values of (0, 0, 255).

The failure detector 220 may detect vertical coordinates and horizontal coordinates of a failure position F of the semiconductor package. The failure of the semiconductor package indicates an open or short state of signal lines of the package substrate or the semiconductor chip. The failure detector 220 may detect the horizontal coordinates of the failure position F of the semiconductor package from the thermographic image of the surface of the semiconductor package, and detects the vertical coordinates of the failure position F of the semiconductor package using the phase difference between a voltage to be described later and the temperature of the surface of the semiconductor package. A method of detecting the horizontal coordinates and the vertical coordinates of the failure position F of the semiconductor package will be described in more detail with reference to FIGS. 5 to 7.

The voltage supply device 230 applies a voltage to the semiconductor package. The voltage supply device 230 may apply a voltage to a micro bump of the package substrate. The voltage that is applied to the semiconductor package may be a square wave, but is not limited thereto. The voltage applied to the semiconductor package may have any waveformso long as the phase of the voltage can be identified.

The input/output device 240 may receive a thermal diffusion coefficient of the semiconductor package from a user. The thermal diffusion coefficient is the thermal characteristic of a material that is indicated by an area per unit time (e.g., $m^2/s$), and represents time for which heat is transferred from a desired (or alternatively, predetermined) distance and cause a temperature change. In the case where the semiconductor package is a multi-chip package in which multiple semiconductor chips are laminated, the input/output device 240 may receive an input of thermal diffusion coefficients of respective layers. The X-ray analyzer 100 may further include a separate memory device (not illustrated) in which previously input thermal diffusion coefficients of the respective layers can be stored.

Figure 4:
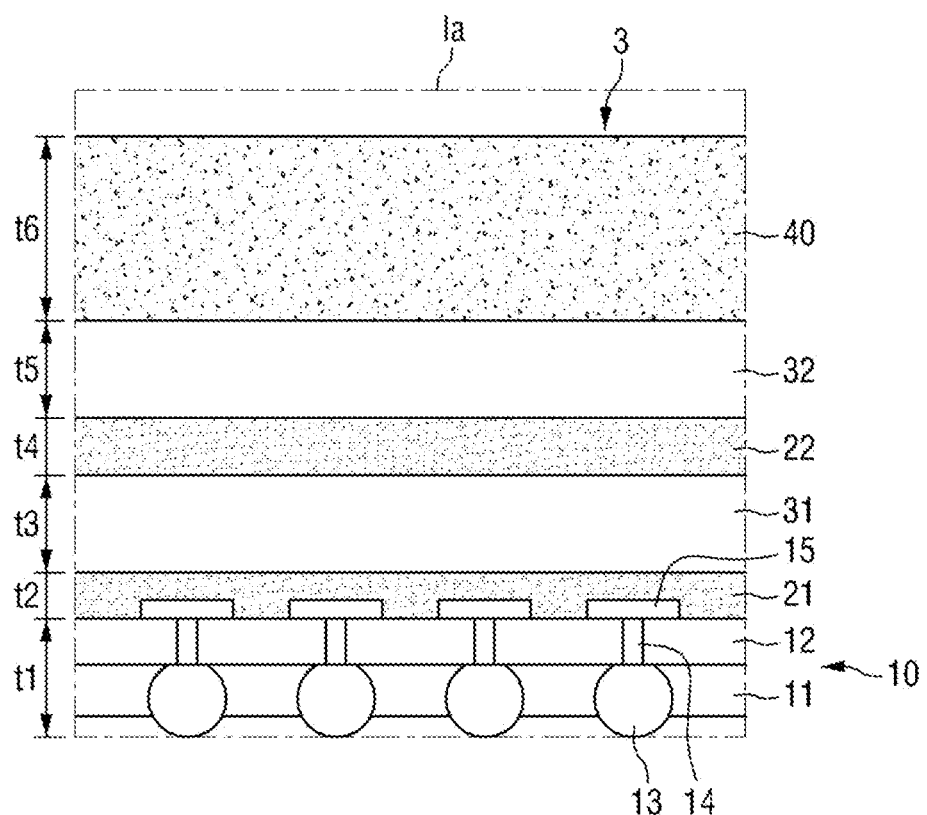
FIG. 4 is a schematic diagram to explain a method of detecting a thickness of a semiconductor package through the X-ray analyzer of FIG. 1.

FIG. 4 is a schematic diagram to explain a method of detecting the thickness of the semiconductor package through the X-ray analyzer of FIG. 1.

Referring to FIG. 4, a semiconductor package 3 includes a first semiconductor chip 31 and a second semiconductor chip 32. However, the present inventive concepts are not limited thereto, but the semiconductor package 3 may include at least one layer. On lower portions of the first semiconductor chip 31 and the second semiconductor chip 32, a first laminate film 21 and a second laminate film 22 may be formed, respectively. The first laminate film 21 and the second laminate film 22 may be a bonding material in the form of a film, and may be used to laminate the first semiconductor chip 31 and the second semiconductor chip 32, respectively. The first laminate film 21 and the second laminate film 22 may be, for example, DAF (Die Attach Films). The package substrate 10 may be formed on a lower portion of the first laminate film 21. The package substrate 10 may include a base substrate 11, a silicon interposer 12, a micro bump 13, a through silicon via 14, and a conductive pad 15. Further, a sealing layer 40 that covers the semiconductor chips 31 and 32 and the laminate films 21 and 22 may be formed. The sealing layer 40 may be used to seal the semiconductor chip to protect the semiconductor chip from an external environment and impact. The sealing layer 40 may be, for example, an EMC (Epoxy Molding Compound).

The image processor 120 may detect the thickness of the semiconductor package 3 from the X-ray image Ia of the semiconductor package 3. For example, the image processor 120 may use the density of the area of the semiconductor package 3 in the X-ray image Ia of the semiconductor package 3. The image processor 120 detects the thicknesses t1 to t6 of the respective layers of the semiconductor package 3 using density values of the respective layers.

For example, the density values of the respective layers in the X-ray image Ia of the semiconductor package 3 can be discriminated from each other as shown in Table 1 below.

TABLE 1

| Layer classification | Density value |
| --- | --- |
| Package substrate (PCB) | 0 to 3 |
| Laminate film (DAF) | 50 to 70 |
| Semiconductor chip (chip) | 20 to 30 |
| Sealing layer (EMC) | 15 |

The image processor 120 may determine the area having the density value of 0 to 3 in the X-ray image Ia of the semiconductor package 3 as the area of the package substrate 10, and may determine the area having the density value of 50 to 70 as the area of the laminate films 21 and 22. Further, the image processor 120 may determine the area having the density value of 20 to 30 as the area of the semiconductor chips 31 and 32, and may determine the area having the density value of 15 as the area of the sealing layer 40. Here, the density values of the respective layer areas may be pre-stored in a memory device (not illustrated) of the X-ray analyzer 100.

Further, because the density values of the respective layers in the X-ray image Ia of the semiconductor package 3 may be discriminated depending on the densities of materials forming the respective layers, the image processor 120 may determine boundaries at which changes of the density values exceed a threshold value in the X-ray image Ia of the semiconductor package 3, and may discriminate the respective layers of the semiconductor package 3 based on the boundary information.

The image processor 120 may discriminate the respective layers in the X-ray image Ia of the semiconductor package 3 according to the above-described method, and may detect the thicknesses t1 to t6 of the respective layers of the semiconductor package 3 using the coordinates of the pixels that constitute the same layer.

In the embodiment of the present invention, the method of detecting the thickness of the semiconductor package may use the densities of the semiconductor package in the X-ray image of the semiconductor package. However, the method of detecting the thickness of the semiconductor package from the X-ray image of the semiconductor package is not limited thereto, but various methods may be used. The detailed description of such methods will be omitted.

Figure 5:
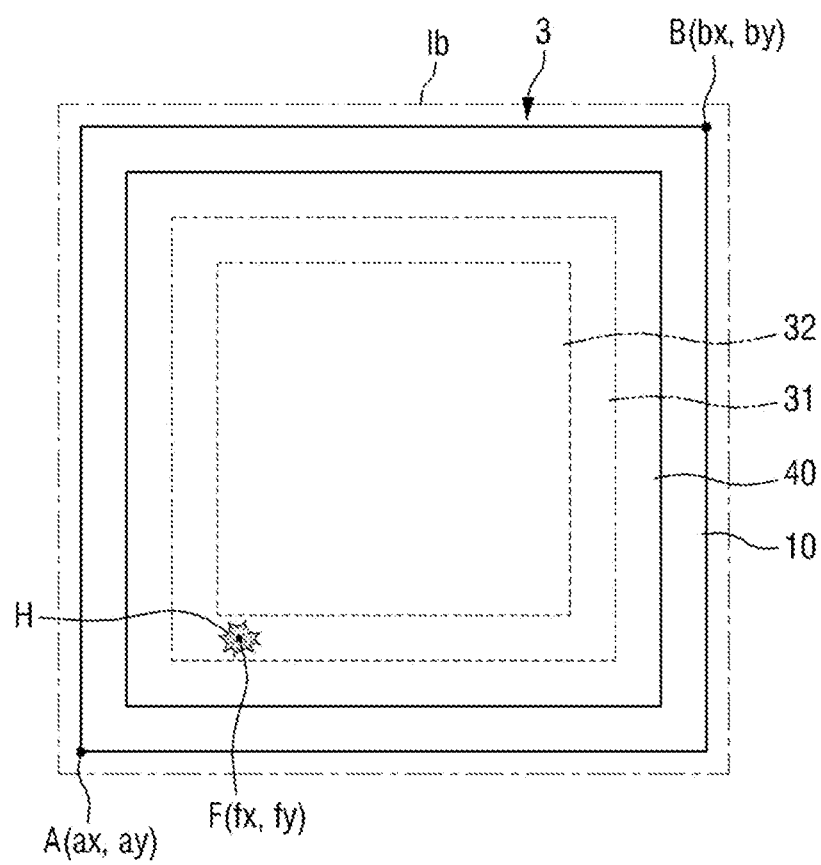
FIG. 5 is a schematic diagram to explain a method of detecting horizontal coordinates of a failure position of a semiconductor package using the thermal reaction analyzer of FIG. 1.

FIG. 5 is a schematic diagram to explain a method of detecting horizontal coordinates of the failure position of the semiconductor package using the thermal reaction analyzer of FIG. 1.

Referring to FIG. 5, on a thermographic image Ib on the upper surface of the semiconductor package 3, the second semiconductor chip 32, the first semiconductor chip 31, and the package substrate 10, which have been described in detail with reference to FIG. 4, may be shown. On the thermographic image Ib of the semiconductor package 3, the area of the semiconductor package 3 and its outer area may be discriminated from each other by their pixel values. The area of the pixel having a density value that is larger than the threshold value in the thermographic image Ib of the semiconductor package 3 may be discriminated as the area of the semiconductor package 3, and the area of the pixel having a density value that is smaller than the threshold value may be discriminated as the outer area. The area of the semiconductor package 3 in the thermographic image Ib of the semiconductor package 3 may be defined by, for example, a left lower pixel A (ax, ay) and a right upper pixel B (bx, by).

The voltage supply device 230 may apply voltage to the semiconductor package 3, and heat H may be generated in the failure position F of the semiconductor package 3 due to the applied voltage. The heat H generated in the failure position F of the semiconductor package 3 may be transferred in the direction of the upper surface of the semiconductor package 3, and the temperature change due to the heat H transferred from the failure position F of the semiconductor package 3 may occur on the upper surface of the semiconductor package 3.

The failure detector 220 may detect the horizontal coordinates (fx, fy) of the failure position F of the semiconductor package 3 from the thermographic image Ib on the upper surface of the semiconductor package 3. The change due to the heat H transferred from the failure position F of the semiconductor package 3 may occur in the thermographic image Ib on the upper surface of the semiconductor package 3. The failure detector 220 may detect the coordinates of the pixel having the highest temperature in the thermographic image Ib on the upper surface of the semiconductor package 3 as the horizontal coordinates (fx, fy) of the failure position F of the semiconductor package 3. In the case where the temperature distribution of the semiconductor package 3 is displayed with colors on the thermographic image Ib of the semiconductor package 3, the pixel having the highest temperature may have, for example, RGB values of (255, 0, 0).

Figure 6:
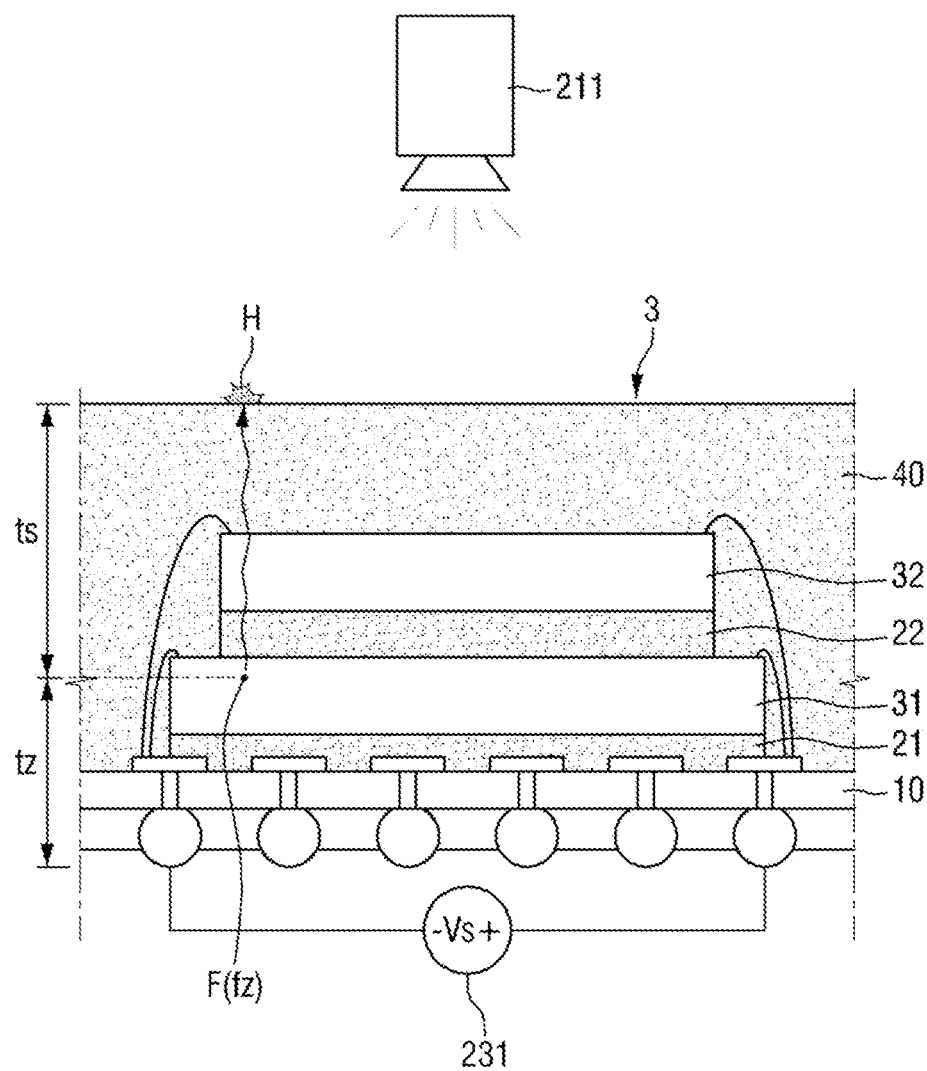
FIGS. 6 and 7 are schematic diagrams to explain a method of detecting vertical coordinates of a failure position of a semiconductor package using the thermal reaction analyzer of FIG. 1.
Figure 7:
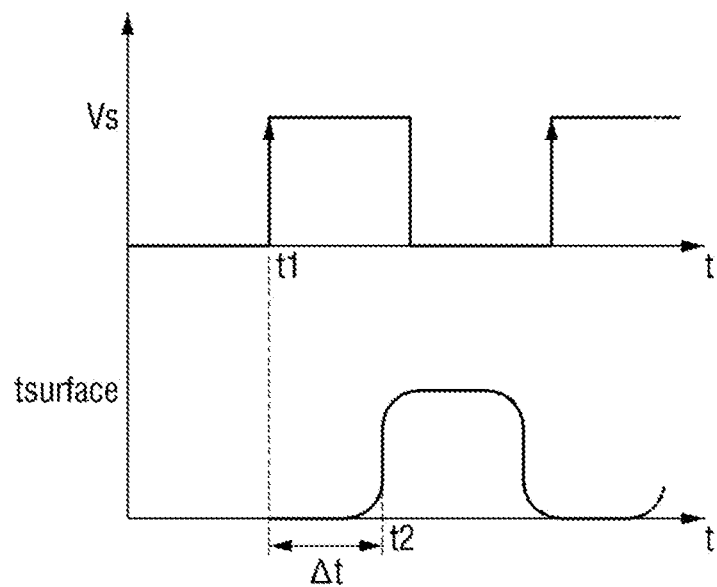

FIGS. 6 and 7 are schematic diagrams to explain a method of detecting the vertical coordinates of the failure position of the semiconductor package using the thermal reaction analyzer of FIG. 1.

Referring to FIG. 6, a voltage source 231 of the voltage supply device 230 is connected to the micro bump 13 to apply the voltage to the semiconductor package 3, and the surface of the semiconductor package 3 is photographed using an infrared sensor 211 of the infrared scope 210. As described above, heat H may be generated in the failure position F of the semiconductor package 3 due to the voltage applied to the semiconductor package 3. The heat H generated in the failure position F of the semiconductor package 3 may be transferred to the direction of the upper surface of the semiconductor package 3, and the surface temperature of the semiconductor package 3 may be changed due to the heat H transferred from the failure position F of the semiconductor package 3.

The failure detector 220 detects the vertical coordinates fz of the failure position F of the semiconductor package 3 using the phase difference between the voltage applied to the semiconductor package 3 and the surface temperature of the semiconductor package 3. The change due to the heat H transferred from the failure position F of the semiconductor package 3 may appear in the thermographic image on the upper surface of the semiconductor package 3. The failure detector 220 may detect the surface temperature of the semiconductor package 3 from the thermographic image on the upper surface of the semiconductor package 3.

Referring to FIG. 7, the voltage Vs that is applied to the semiconductor package 3 by the voltage supply device 230 may be a square wave. The voltage Vs applied to the semiconductor package 3 shows a rising edge at t1, and the surface temperature tsurface of the semiconductor package 3 shows a rising edge at t2. For example, the phase difference between the voltage Vs applied to the semiconductor package 3 and the surface temperature tsurface of the semiconductor package 3 may correspond to $\Delta t$ (i.e., t2−t1).

According to an example embodiment, the phase difference may be obtained on the basis of the rising edge of the voltage applied to the semiconductor package and the rising edge of the surface temperature of the semiconductor package. However, the method for obtaining the phase difference between the voltage applied to the semiconductor package and the surface temperature of the semiconductor package is not limited thereto, but various known methods may be used. The detailed description of such known methods will be omitted.

The failure detector 220 may detect the distance ts between the failure position F of the semiconductor package 3 and the upper surface of the semiconductor package 3 using $\Delta t$ and the thermal diffusion coefficient of the semiconductor package 3. For example, the failure detector 220 may use the respective thermal diffusion coefficients of the package substrate 10, the laminate films 21 and 22, the semiconductor chips 31 and 32, and the sealing layer 40.

The failure detector 220 may detect the accurate vertical coordinates fz of the failure position F of the semiconductor package 3. If it is assumed that a reference line of the vertical coordinate system is a bottom surface of the micro bump 13 of the semiconductor package 3, the vertical coordinates fz of the failure position F of the semiconductor package 3 may be detected as a distance tz that is obtained by subtracting the distance ts (i.e., a distance between the failure position F of the semiconductor package 3 and the upper surface of the semiconductor package 3) from the overall thickness of the semiconductor package 3 (i.e., a distance between the bottom surface and the upper surface of the semiconductor package 3). The failure detector 220 may detect the relative vertical coordinates of the layer on which the failure has occurred and the failure position F of the corresponding layer, using the thicknesses of the respective layers of the semiconductor package 3.

Figure 8:
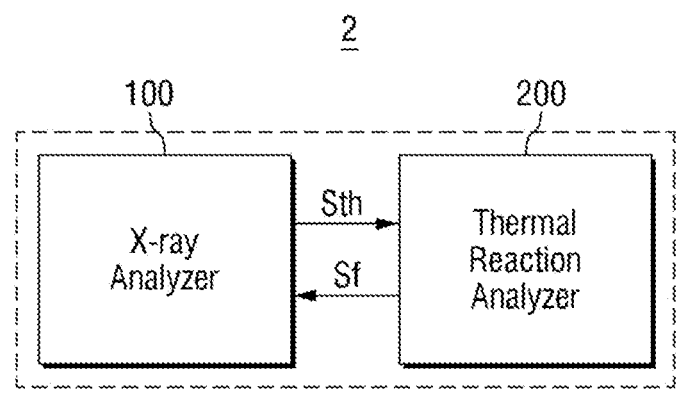
FIG. 8 is a schematic block diagram illustrating the configuration of a test apparatus for a semiconductor package according to another example embodiment.

FIG. 8 is a schematic block diagram illustrating the configuration of a test apparatus for a semiconductor package according to another example embodiment. For convenience of explanation, different points from the configuration illustrated in FIG. 1 will be described in detail.

Referring to FIG. 8, a test apparatus 2 for a semiconductor package according to this embodiment includes the X-ray analyzer 100 and the thermal reaction analyzer 200.

The X-ray analyzer 100 may acquire the X-ray image of the semiconductor package, and may detect the thickness of the semiconductor package from the X-ray image of the semiconductor package. The X-ray analyzer 100 may transmit the detected thickness information Sth of the semiconductor package to the thermal reaction analyzer 200. The X-ray analyzer 100 may receive the coordinate information Sf of the failure position F of the semiconductor package from the thermal reaction analyzer 200.

The X-ray analyzer 100 may include the X-ray scope 110, the image processor 120, and the display panel 130. The X-ray scope 110 and the image processor 120 may be the same as those as described above with reference to FIG. 2.

The display panel 130 may display the X-ray image of the semiconductor package. The display panel 130 may display the X-ray image on which the failure position F of the semiconductor package is shown. The display panel 130 may display the failure position F on the three-dimensional X-ray image of the semiconductor package.

The thermal reaction analyzer 200 may receive the thickness information Sth of the semiconductor package from the X-ray analyzer 100. The thermal reaction analyzer 200 may apply voltage to the semiconductor package, and may detect the failure position F of the semiconductor package using the surface temperature of the semiconductor package and the thickness of the semiconductor package. The thermal reaction analyzer 200 transmits the coordinate information Sf of the detected failure position F of the semiconductor package to the X-ray analyzer 100.

The thermal reaction analyzer 200 may include the infrared scope 210, the failure detector 220, the voltage supply device 230, and the input/output device 240. The infrared scope 210, the failure detector 220, the voltage supply device 230, and the input/output device 240 may be the same as those as described above with reference to FIG. 3.

Figure 9:
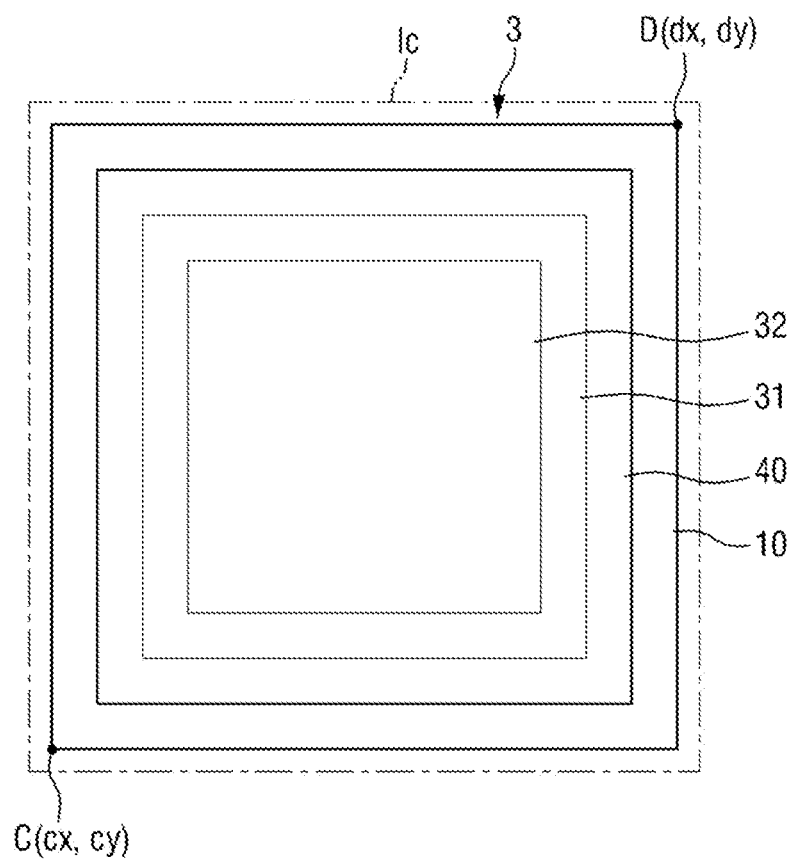
FIG. 9 is a schematic diagram illustrating an X-ray image of a semiconductor package acquired by the X-ray analyzer of FIG. 8.

FIG. 9 is a schematic diagram illustrating an X-ray image of the semiconductor package acquired by the X-ray analyzer of FIG. 8.

Referring to FIG. 9, on an X-ray image Ic of the semiconductor package 3, the second semiconductor chip 32, the first semiconductor chip 31, and the package substrate 10 as described above with reference to FIG. 4 may be displayed. The laminate films 21 and 22 of the semiconductor package 3, the sealing layer 40, and the configurations 11 to 15 of the package substrate may be displayed according to the characteristic of the X-ray image. However, for convenience of explanation, the display of the configurations 11 to 15 will be omitted. On the X-ray image Ic of the semiconductor package 3, the area of the semiconductor package 3 and an outer area thereof may be discriminated by their density values. On the X-ray image Ic of the semiconductor package 3, the area of the pixel having the density value that is larger than the threshold value may be discriminated as the area of the semiconductor package 3, and the area of the pixel having the density value that is smaller than the threshold value may be discriminated as the outer area. The area of the semiconductor package 3 in the thermographic image Ic of the semiconductor package 3 may be defined as, for example, a left lower pixel C (cx, cy) and a right upper pixel D (dx, dy).

On the other hand, although FIG. 9 shows the X-ray image of the upper surface of the semiconductor package as an example, the X-ray image can be acquired in the same manner with respect to each single layer of the semiconductor package.

Figure 10:
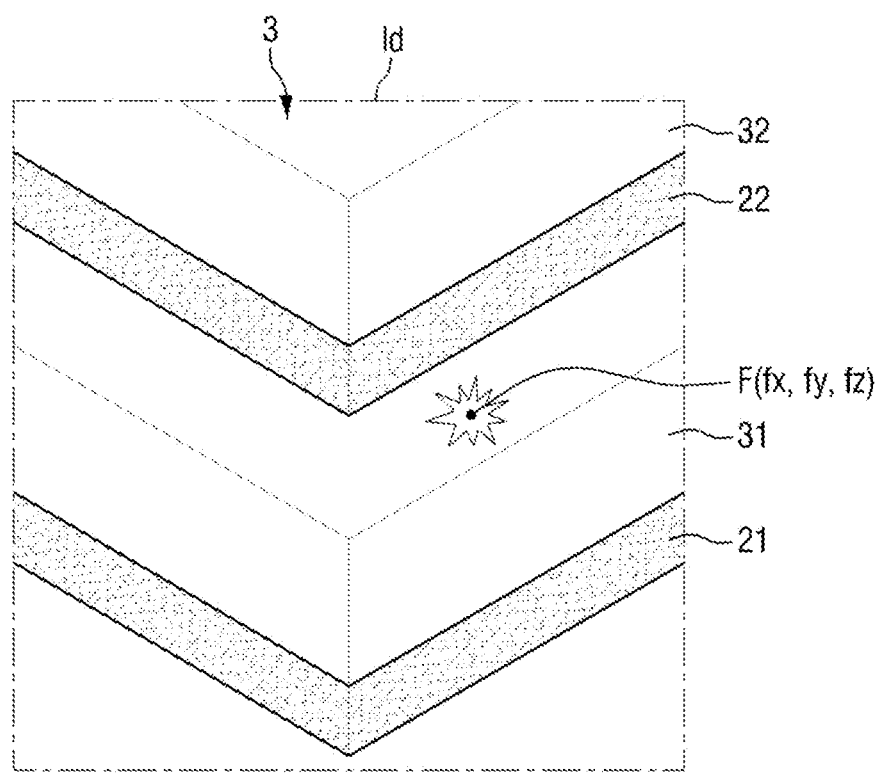
FIG. 10 is a schematic diagram illustrating a failure position that appears on an X-ray image of a semiconductor package acquired by the X-ray analyzer of FIG. 8.

FIG. 10 is a schematic diagram illustrating the failure position that appears on the X-ray image of the semiconductor package acquired by the X-ray analyzer of FIG. 8.

Referring to FIG. 10, the failure position F of the semiconductor package may be displayed on the X-ray image Id of the semiconductor package 3, which is displayed on the display panel 130. For example, the X-ray image Id of the semiconductor package 3 may be a three-dimensional X-ray image. The display of the failure position F of the semiconductor package 3 on the X-ray image Id includes marking of the failure position F of the semiconductor package 3 on the X-ray image Id so that the user can identify the failure position F. For example, in the vicinity of the failure position F of the semiconductor package 3, the three-dimensional coordinates (fx, fy, fz) of the failure position F may be displayed together. The three-dimensional coordinates (fx, fy, fz) of the failure position F of the semiconductor package 3 may include the vertical coordinates and the horizontal coordinates of the failure position F.

In order to display the failure position F of the semiconductor package 3 received from the thermal reaction analyzer 200 on the X-ray image Id of the semiconductor package 3, the image processor 120 makes the coordinate system of the X-ray image of the semiconductor package 3 and the coordinate system of the thermographic image of the semiconductor package 3 match each other. For example, the image processor 120 can match multiple coordinate systems by standardizing C (cx, cy) and D (dx, dy) that define the area of the semiconductor package 3 in the X-ray image of the semiconductor package 3 and A (ax, ay) and B (bx, by) that define the area of the semiconductor package 3 in the thermographic image of the semiconductor package 3 as (0, 0) and (1, 1). The method of matching the multiple coordinate systems is not limited thereto, but various methods except for the above-described method may be used. The detailed description of such methods will be omitted.

According to the example embodiments as described above, because the vertical coordinates of the failure position of the semiconductor package may be detected using the actual thickness of the semiconductor package detected using the X-ray image rather than the thickness on the specification of the semiconductor package, the failure position of the semiconductor can be more accurately detected in spite of the process deviation. Further, because the semiconductor package can be tested simultaneously by using the X-ray analyzer 100 and the thermal reaction analyzer 200, and the failure position of the semiconductor package may be directly confirmed on the X-ray image, the analysis time can be shortened and the failure position of the semiconductor package can be promptly detected.

While the example embodiments have been particularly shown and described, those skilled in the art will appreciate that variations and modifications can be made to the example embodiments without departing from the principles of the present inventive concepts. Therefore, the disclosed example embodiments of the invention are used in a generic and descriptive sense only and not for purposes of limitation.

What is claimed is:

1. A test apparatus for a semiconductor package comprising:
    an X-ray analyzer configured to acquire an X-ray image of the semiconductor package and detect a thickness of the semiconductor package from the X-ray image; and
    a thermal reaction analyzer configured to apply voltages to the semiconductor package and detect a failure position of the semiconductor package using a surface temperature of the semiconductor package and the detected thickness of the semiconductor package.

2. The test apparatus for a semiconductor package of claim 1, wherein the X-ray analyzer comprises an image processor configured to detect the thickness of the semiconductor package using a density of an area of the semiconductor package in the X-ray image.

3. The test apparatus for a semiconductor package of claim 2, wherein the semiconductor package includes at least one layer, and the image processor is configured to detect a thickness of the at least one layer using density information of the at least one layer in the X-ray image.

4. The test apparatus for a semiconductor package of claim 1, wherein the thermal reaction analyzer comprises a failure detector configured to detect vertical coordinates of the failure position using a phase difference between the voltages applied to the semiconductor package and the surface temperature of the semiconductor package.

5. The test apparatus for a semiconductor package of claim 4, wherein the thermal reaction analyzer comprises an infrared scope configured to acquire a thermographic image on a surface of the semiconductor package, and the failure detector is configured to detect the surface temperature of the semiconductor package from the thermographic image.

6. The test apparatus for a semiconductor package of claim 4, wherein the failure detector is configured to detect the vertical coordinates of the failure position using a thermal diffusion coefficient of the semiconductor package.

7. The test apparatus for a semiconductor package of claim 1, wherein the thermal reaction analyzer comprises an infrared scope configured to acquire a thermographic image on the surface of the semiconductor package, and a failure detector configured to detect horizontal coordinates of the failure position from the thermographic image.

8. The test apparatus for a semiconductor package of claim 7, wherein the failure detector is configured to detect coordinates of a pixel having a maximum pixel value in the thermographic image as the horizontal coordinates of the failure position.

9. The test apparatus for a semiconductor package of claim 1, wherein the X-ray image is a three-dimensional X-ray image of the semiconductor package.

10. A test apparatus for a semiconductor package comprising:
    an X-ray analyzer configured to detect a thickness of the semiconductor package, the X-ray analyzer including,
        an X-ray scope configured to acquire an X-ray image of the semiconductor package,
        an image processor configured to detect a thickness of the semiconductor package from the X-ray image, and
        a display unit configured to display the X-ray image designating a failure position thereon; and
    a thermal reaction analyzer configured to detect the failure position of the semiconductor package, the thermal reaction analyzer including,
        a voltage supply device configured to apply voltages to the semiconductor package,
        an infrared scope configured to acquire a thermographic image on a surface of the semiconductor package, and
        a failure detector configured to detect vertical coordinates of the failure position using the detected thickness of the semiconductor package and a phase difference between the voltages applied to the semiconductor package and a surface temperature of the semiconductor package, and detect horizontal coordinates of the failure position from the thermographic image.

11. The test apparatus for a semiconductor package of claim 10, wherein the semiconductor package includes at least one layer, and the image processor is configured to detect a thickness of the at least one layer using density information of the at least one layer in the X-ray image.

12. The test apparatus for a semiconductor package of claim 10, wherein the failure detector is configured to detect the surface temperature of the semiconductor package from the thermographic image.

13. The test apparatus for a semiconductor package of claim 10, wherein the failure detector is configured to detect the vertical coordinates of the failure position using a thermal diffusion coefficient of the semiconductor package.

14. The test apparatus for a semiconductor package of claim 13, wherein the failure detector is configured to detect coordinates of a pixel having a maximum pixel value in the thermographic image as the horizontal coordinates of the failure position.

15. The test apparatus for a semiconductor package of claim 10, wherein the X-ray image is a three-dimensional X-ray image of the semiconductor package.

16. A test apparatus for a semiconductor package comprising:
an X-ray analyzer configured to detect at least one of a thickness of the semiconductor package and thicknesses of layers of the semiconductor package using an X-ray image of the semiconductor package and density information of the layers; and
a thermal reaction analyzer configured to apply voltages to the semiconductor package and detect a failure position of the semiconductor package using a surface temperature of the semiconductor package and the at least one of the detected thickness transmitted from the X-ray analyzer.

17. The test apparatus for a semiconductor package of claim 16, wherein the thermal reaction analyzer includes:
an infrared scope configured to acquire a thermographic image of a surface of the semiconductor package; and
a failure detector configured to detect a horizontal coordinate and a vertical coordinate of the failure position of the semiconductor package.

18. The test apparatus for a semiconductor package of claim 17, wherein the failure detector is configured to detect the horizontal coordinate of the failure position from the thermographic image of the surface of the semiconductor package, and the failure detector is configured to detect a vertical coordinate of the failure position using a phase difference between the voltages applied to the semiconductor package and the surface temperature of the semiconductor device.

19. The test apparatus for a semiconductor package of claim 17, wherein the failure detector is configured to detect a vertical coordinate of the failure position using thermal diffusion coefficient information of layers forming the semiconductor package and a phase difference between the voltages applied to the semiconductor package and the surface temperature of the semiconductor device.

20. The test apparatus for a semiconductor package of claim 16, wherein the X-ray analyzer includes:
an X-ray scope configured to acquire at least one of a two-dimensional and a three-dimensional X-ray image; and
an image processor configured to detect the at least one of a thickness of the semiconductor package and thicknesses of layers of the semiconductor package using the density information of the layers.

* * * * *